US008257743B2

(12) United States Patent
Yoo et al.

(10) Patent No.: US 8,257,743 B2
(45) Date of Patent: Sep. 4, 2012

(54) MULTI-FUNCTIONAL NANOPARTICLES PARTIALLY-DEPOSITED WITH GOLD FILM

(75) Inventors: Kyung Hwa Yoo, Seoul (KR); Jeon Soo Shin, Seoul (KR); Seungjoo Haam, Seoul (KR); Hui Yul Park, Goyang-si (KR); Jaemoon Yang, Gunpo-si (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 459 days.

(21) Appl. No.: 12/443,004

(22) PCT Filed: Jun. 29, 2007

(86) PCT No.: PCT/KR2007/003182
§ 371 (c)(1),
(2), (4) Date: Mar. 26, 2009

(87) PCT Pub. No.: WO2008/002101
PCT Pub. Date: Jan. 3, 2008

(65) Prior Publication Data
US 2010/0028453 A1    Feb. 4, 2010

(30) Foreign Application Priority Data
Jun. 30, 2006    (KR) ........................ 10-2006-0060678

(51) Int. Cl.
*A61K 9/14*    (2006.01)
*A61K 33/24*    (2006.01)
(52) U.S. Cl. ............. 424/489; 424/649; 607/1; 977/773
(58) Field of Classification Search ........................ None
See application file for complete search history.

(56) References Cited

U.S. PATENT DOCUMENTS

| | | | |
|---|---|---|---|
| 6,060,256 A | 5/2000 | Everhart et al. | |
| 6,162,926 A | 12/2000 | Murphy et al. | |
| 6,660,381 B2 * | 12/2003 | Halas et al. | 428/403 |
| 6,685,986 B2 * | 2/2004 | Oldenburg et al. | 427/214 |
| 6,933,331 B2 | 8/2005 | Yadav et al. | |
| 2002/0061363 A1 * | 5/2002 | Halas et al. | 427/217 |
| 2002/0103517 A1 * | 8/2002 | West et al. | 607/88 |
| 2003/0174384 A1 * | 9/2003 | Halas et al. | 359/296 |
| 2005/0208098 A1 * | 9/2005 | Castro et al. | 424/423 |
| 2007/0292495 A1 * | 12/2007 | Ludwig et al. | 424/450 |

OTHER PUBLICATIONS

International Search Report and Written Opinion dated Oct. 22, 2007, issued in PCT/KR2007/003182. Naomi Halas "The Optical Properties of Nanoshells", Optics and Photonics News, vol. 13, Issue 8, pp. 26-30 (2002), Gold Covered Nanoshells, Business Week, May 21, 2001.

* cited by examiner

*Primary Examiner* — Frederick Krass
*Assistant Examiner* — Isaac Shomer
(74) *Attorney, Agent, or Firm* — Bryan Cave LLP

(57) ABSTRACT

Disclosed herein are multifunctional nanoparticles, comprising: polymer nanoparticles formed by loading a drug into a polymer; a gold thin film deposited on a portion of the surface of the polymer nanoparticles; and an antibody to a substance expressed on the surface of a cell to which the drug is to be delivered, the antibody being conjugated to the gold thin film. Also disclosed is a method for preparing multifunctional nanoparticles, the method comprising the steps of: loading a drug into a polymer to prepare polymer nanoparticles; depositing a portion of the surface of the polymer nanoparticles with a gold thin film; conjugating to the gold thin film an antibody to a substance expressed on the surface of a cell to which the drug is to be delivered; and separating from the resulting nanoparticles those in which a portion of the surface of the polymer nanoparticles is deposited with the gold thin film and conjugated with the antibody. Furthermore, disclosed are a composition containing the multifunctional nanoparticles and a method for diagnosing and treating disease using the composition.

5 Claims, 19 Drawing Sheets

US 8,257,743 B2

MULTI-FUNCTIONAL NANOPARTICLES PARTIALLY-DEPOSITED WITH GOLD FILM

CROSS-REFERENCE TO RELATED APPLICATIONS

The present application is a U.S. National Phase patent application under 35 U.S.C. §371 of International Application No. PCT/KR2007/003182, filed Jun. 29, 2007, which claims priority to South Korean Patent Application No. 10-2006-0060678, filed Jun. 30, 2006, both of which are expressly incorporated herein by reference.

TECHNICAL FIELD

The present invention relates to multifunctional nanoparticles, and more particularly to multifunctional nanoparticles, comprising: polymer nanoparticles, formed by loading a drug into a polymer; a gold thin film, deposited on a portion of the surface of the polymer nanoparticles; and an antibody to a substance expressed on the surface of a cell to which the drug is to be delivered, the antibody being conjugated to the gold thin film, as well as a preparation method thereof, a composition containing the multifunctional nanoparticles, and a method for diagnosing and treating disease using the composition.

BACKGROUND ART

A targeted drug delivery method is a drug delivery method that allows a drug to be accumulated selectively and quantitatively in a target organ or tissue regardless of administration methods and sites. This delivery method can maximize the therapeutic effect of a drug by increasing the concentration of the drug in the target site, while it can minimize side effects by reducing the concentration of the drug in non-target tissues and organs. In addition, it can significantly reduce not only the amount of therapeutic drug required to achieve a therapeutic effect, but also the cost required for treatment.

There are two strategies for the targeted drug delivery. One of them is to concentrate drug carrier into specific site by controlling it physically. There have been developed magnetic nanoparticles, in which a magnetic substance, such as magnetite, and a drug are encapsulated with a polymer. When such magnetic nanoparticles are injected into a patient, and then an external magnetic field is artificially applied to the target site, the nanoparticles are localized to the target site, so that the drug loaded in the nanoparticles is released, thus exhibiting therapeutic effects. However, in this method, it is required to know the accurate location of disease in advances and the instrument to generate high magnetic field locally is also needed.

The other is to make drug carrier delivered to target site by conjugating a ligand such as antibody, glycoprotein, etc., which can bind to a substance, which is called as a receptor such as antigen, receptor protein, etc., on the surface of a cell to which the drug is to be delivered, to drug carrier. Due to using specific interaction between an antibody and antigen, this method has a merit to deliver drug carrier to unknown site to which the drug is to be delivered accurately. However, in order to use antibody targeting method, drug carrier is able to contain target drug, to be conjugated to target antibody easily and has a good bio-distribution. As one method for this method, there has been developed a targeted drug delivery system, in which a drug is loaded in a virus, such as an adenovirus or a retrovirus. However, the method for delivering drugs using viruses has problems in that the kind of drug is limited to protein or nucleic acid, and particularly in that viruses cause host immune reactions, which increase side effects instead of therapeutic effects.

And there has been developed a targeted drug delivery system, in which a drug is loaded in biocompatible polymer, and an antibody to a substance present on the surface of a cell to which the drug is to be delivered, is bound to the surface of polymer. Because polymer, which is compatible to body and has low immunity, is used, this drug carrier has a better bio-distribution than virus carrier. However this method to use polymer have a problem not to control the drug release pattern optionally, because the drug release pattern is dependent on polymer degradation.

Recently, since it became known that optical transmission through tissue is optimized in the near-infrared region (NIR) (i.e., 800-1200 nm), near-infrared resonant nanoshells, such as gold-coated nanoshells ($Au_2S$) (Averitt, R. D. et al. *Phys. Rev. Lett.* 1997, vol. 78, p. 4217), silica-gold nanoshell particles (Loo, C. et al. *Tech. in Cancer Res. & Treatment,* 2004, vol. 3, p. 33) and hollow gold nanoshells (Chen, J. et al. *Nano Lett.* 2005, vol. 5, p. 473), have been widely studied in the biomedical field.

Generally, the surface plasmon-resonance frequency of solid metal nanoparticles is located in the visible range. However, metallic nanoshells show the flexibility of regulating the resonance frequency from the visible range to the NIR range, as the thickness thereof is varied. Since such metallic nanoshells strongly absorb NIR light and convert the optical energy of the absorbed light to heat, they can be used in thermal therapy and photothermally modulated drug delivery.

L. R. Hirsh et al. demonstrated that silica-gold nanoshells can be used to deliver therapeutically effective heat in an amount capable of killing only target cells, without causing damage to normal cells through excessive local heating (Hirsh, L. R. et al. *Proc. Natl. Acad. Sci. USA* 2003, vol. 100, p. 13549). Also, S. R. Sershen et al. demonstrated that a poly-NIPAAm-co-AAm/AU—$Au_2S$ nanoshell composite performs reversible phase transition in response to NIR radiation and promotes drug release from the composite hydrogel immediately after NIR radiation (Sershen, S. R. et al. *J. Biomed. Mater. Res.* 2000, vol. 51, p. 293).

However, because the NIPAAm-co-AAm hydrogel contains acrylamide (AAm), known to be a toxic substance, it has a problem of low biocompatibility. In particular, acrylamide is known to have adverse affects on male reproductive organs and renal or nervous cells, and is designated a presumed carcinogenic substance in the Industrial Safety and Health Act.

SUMMARY OF THE INVENTION

Accordingly, the present inventors have made efforts to provide a more biocompatible, targeted drug delivery system and, as a result, prepared nanoparticles by loading a drug into a polymer, depositing a gold thin film on a portion of the surface of the polymer, and conjugating an antibody to the gold thin film. Also, the present inventors have found that the nanoparticles are concentrated on a target site by the antibody, and when the target site is irradiated with near infrared light, heat is generated by the gold thin film to kill cells in the target site and promote the degradation of the polymer to accelerate the release of the drug, thus doubling the efficacy of the drug. On the basis of this finding, the present invention has been completed.

In one aspect, the present invention provides multifunctional nanoparticles, comprising: polymer nanoparticles formed by loading a drug into a polymer; a gold thin film deposited on a portion of the surface of the polymer nanoparticles; and an antibody to a substance expressed on the surface of a cell to which the drug is to be delivered, the antibody being conjugated to the gold thin film.

In another aspect, the present invention provides a method for preparing multifunctional nanoparticles, comprising the steps of: (1) loading a drug into a polymer to prepare polymer nanoparticles; (2) depositing a portion of the surface of the polymer nanoparticles with a gold thin film; (3) conjugating to the gold thin film an antibody to a protein expressed on the surface of a cell to which the drug is to be delivered; and (4) separating from the resulting nanoparticles those in which a portion of the surface of the polymer nanoparticles is deposited with the gold thin film and is conjugated with the antibody.

In still another aspect, the present invention provides a composition for delivering a drug to a target site, the composition comprising: multifunctional nanoparticles, comprising: polymer nanoparticles, formed by loading a drug into a polymer; a gold thin film, deposited on a portion of the surface of the polymer nanoparticles; and an antibody to a substance expressed on the surface of a cell to which the drug is to be delivered, the antibody being conjugated to the gold thin film; and a pharmaceutically acceptable carrier.

In yet another aspect, the present invention provides a therapeutic method, comprising: (1) injecting into a subject the inventive composition for delivering a drug to a target site; (2) concentrating the multifunctional nanoparticles at the target site; and (3) irradiating the target site with near-infrared light to generate heat in the target site, so as to kill cells present in the target site and accelerate the release of the drug, thus doubling the efficacy of the drug in the target site.

In yet still another aspect, the present invention provides a method for diagnosing and treating disease, the method comprising the stops of: (1) injecting into a subject the inventive composition for delivering a drug to a target site; (2) sensing a signal emitted by the multifunctional nanoparticles from the subject to identify the target site; and (3) irradiating the target site with near-infrared light to generate heat, so as to kill cells present in the target site and accelerate the release of the drug, thus treating the target site.

DETAILED DESCRIPTION OF THE INVENTION

Figure 1A:
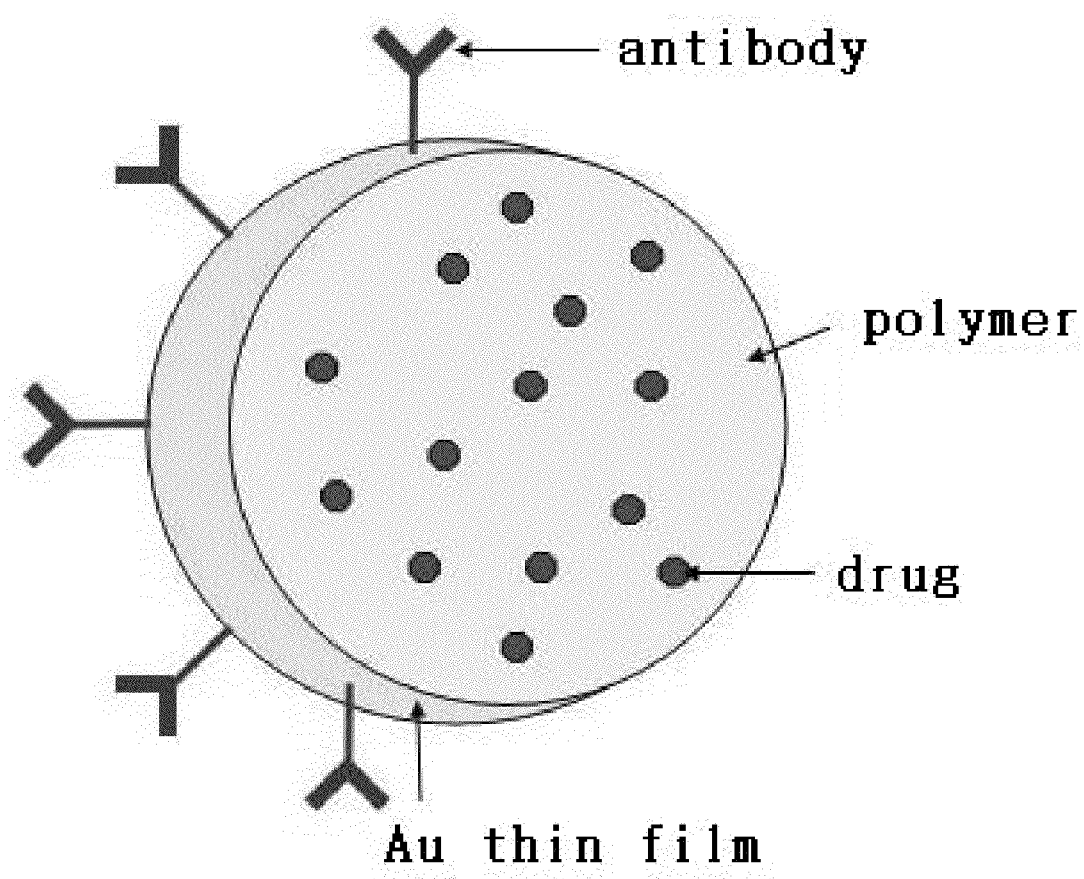
FIG. 1A schematically shows multifunctional nanoparticles according to one embodiment of the present invention.

The present invention relates to multifunctional nanoparticles, comprising: polymer nanoparticles, formed by loading a drug into a polymer; a gold thin film, deposited on a portion of the surface of the polymer nanoparticles; and an antibody to a substance expressed on the surface of a cell to which the drug is to be delivered, the antibody being conjugated to the gold thin film (see FIG. 1A). To more clearly describe the multifunctional nanoparticles according to the present invention, the following terms will now be defined.

As used herein, the term "polymer nanoparticles" means particles comprising a polymer containing a drug, and may be expressed as the kind of polymer, plus "nanoparticles", for convenience. For example, if the kind of polymer is poly (lactic-co-glycolic acid) (PLGA), the term "polymer nanoparticles" is expressed as "PLGA nanoparticles".

As used herein, the term "gold thin film-polymer nanoparticles" means particles comprising a gold thin film coated on a portion of the surface of the polymer nanoparticles and may be expressed as "gold thin film", plus the kind of polymer, followed by "nanoparticles", for convenience. For example, if the kind of polymer is poly(lactic-co-glycolic acid) (PLGA), "gold thin film-polymer nanoparticles" is expressed as "gold thin film-PGA nanoparticles".

As used herein, the term "antibody-gold thin film-polymer nanoparticles" means particles comprising an antibody conjugated to the surface of the gold thin film-polymer nanoparticles, and may be expressed as the kind of antibody, plus "gold thin film", then the kind of polymer, followed by "nanoparticles", for convenience. For example, if the antibody is a CD4 antibody, and the polymer is poly(lactic-co-glycolic acid) (PLGA), the term "antibody-gold thin film-polymer nanoparticles" is expressed as "CD4 antibody-gold thin film-PLGA nanoparticles". Also, the term "antibody-gold thin film-polymer nanoparticles" may be used interchangeably with the term "multifunctional nanoparticles" in the present invention.

The kind and chemical composition of the drug present within the multifunctional nanoparticles according to the present invention are not specifically limited, and may be varied depending on the disease to be treated. Herein, it should be understood that the expression "the drug is loaded in the multifunctional nanoparticles" means that the drug is not located in the very middle of the multifunctional nanoparticles, but rather is located at any position within the polymer nanoparticles. In particular, because the multifunctional nanoparticles according to the present invention can concentrate the drug at the target site, they will be useful for delivering drugs, such as anticancer drugs, immunosuppressive drugs and anti-inflammatory drugs, the clinical use of which is limited due to side effects.

For example, in the present invention, as an anticancer drug, cisplatin, carboplatin, chlorambucil, busulfan, cyclophosphamide, doxorubicin, bleomycin, mechlorethamine, dactinomycin, taxol, vincristine or vinblastine may be used; as an immunosuppressive drug, bromouracil (BUdR), fluorouracil (FUdR), cyclophosphamide, cortisone, predonisolone, 6-mercaptopurin, actinomycin D or dexamethasone may be used; and as an anti-inflammatory drug, naproxen, diclofenac, piroxicam, ibuprofen, azapropazone, fenoprofen, flurbiprofen, pirazolac, bromfenac or ampiroxicam may be used, but the scope of the present invention is not limited thereto.

As the polymer, which encapsulates (i.e., coats) the drug, any biodegradable polymer known in the art may be used. For example, one selected from the group consisting of polystyrene, polyethyleneimine, polyphosphazene, polylactide, polylactide-co-glycolide, polycaprolactone, polyanhydride, polymaleic acid and its derivatives, polyalkylcyanoacrylate, polyanhydride oxybutyrate, polycarbonate, polyorthoester, polyethylene glycol, poly-L-lysine, polyglycolide, polymethylmethacrylate, polyvinylpynolidone, and copolymers thereof, may be used. Such polymers are known to show not only low toxicity, but also excellent biocompatibility (A. J. Domb, et al. *Handbook of biodegradable polymers*, Harwood academic publishers, USA, 1997). In the present invention, it is preferred to use PLGA, approved by the USA FDA.

The gold thin film deposited on the polymer surface functions to convert near-infrared photoenergy into thermal energy (referred to also as "photothermal energy"), so as to kill cells (e.g., cancer cells) in the target site and promote the degradation of the polymer to accelerate the release of the drug located in the polymer. In particular, the multifunctional nanoparticles according to the present invention are characterized in that the gold thin film is deposited only on a portion of the surface of the polymer nanoparticles. The portion of the polymer nanoparticle particle on which the gold thin film is not deposited functions as an outlet for the release of the drug. To accomplish this function, the gold thin film is deposited on 10-90%, preferably 20-80%, and more preferably 30-70%, of the entire surface of the polymer nanoparticles. Also, the gold thin film may be made of gold, platinum or an alloy of the two metals.

In the present invention, the thickness of the gold thin film may vary depending on the kind of polymer used. If polystyrene is used as the polymer, the thickness of the gold thin film is preferably more than 14 nm. This is because, in this case, the absorption peak of the multifunctional nanoparticles can be located in the near infrared range, having excellent tissue compatibility (see Example 3A). Meanwhile, if poly(lactic-co-glycolic acid) is used as the polymer, the absorption peak of the multifunctional nanoparticles is located in the near infrared range regardless of the thickness of the gold thin film (see Example 3B).

The antibody, which contributes to concentrating the inventive multifunctional nanoparticles at the target site, may be an antibody to a substance expressed on the surface of a cell to which the drug is to be delivered. In particular, tumor cells express a specific substance (i.e., tumor marker), which is produced little or not at all in normal cells, and a substance (e.g., antibody, antibody variant or peptide) that can bind specifically to such a tumor marker can be introduced into the inventive multifunctional nanoparticles, such that it can be used for the treatment of the tumor. Not only various tumor markers, but also substances capable of binding specifically to these tumor markers, are known in the art to which the present invention pertains. Examples of tumor markers include carcinoembryonic antigens, HER2/neu antigens, prostate-specific membrane antigens and the like. In the present invention, the antibody may be monoclonal or polyclonal, but is preferably monoclonal for the purpose of precise targeting.

Figure 1B:
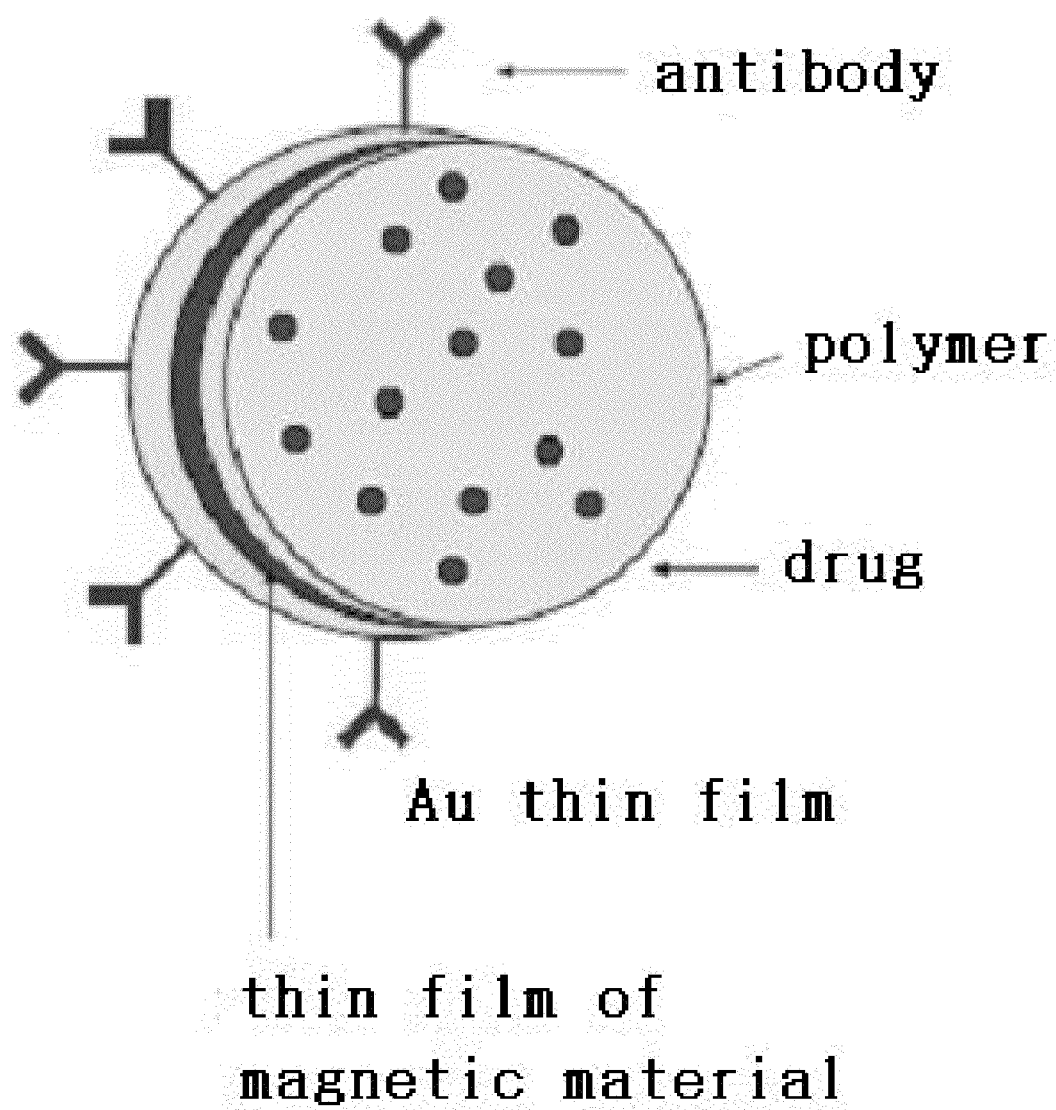
FIG. 1B schematically shows multifunctional nanoparticles according to another embodiment of the present invention.

In another embodiment, the multifunctional nanoparticles according to the present invention comprise: polymer nanoparticles formed by loading a drug into a polymer; a thin film of magnetic material deposited on the surface of the polymer nanoparticles; a gold thin film deposited on a portion of the surface of the magnetic thin film; and an antibody to a substance expressed on the surface of a cell to which the drug is to be delivered, the antibody being conjugated to the surface of the gold thin film (see FIG. 1B). Herein, a gold thin film may also additionally be deposited between the polymer nanoparticles and the magnetic thin film. Because the multifunctional nanoparticles contain the magnetic material, they can be used to diagnose disease.

The drug, the polymer and the gold thin film, which form the multifunctional nanoparticles, are all similar to the above-described drug, polymer and gold thin film, and a relevant description will not be repeated. Herein, as the magnetic material, any magnetic material known in the art may be used, and examples thereof include Co, Mn, Fe, Ni, Gd and the like. The method of forming the thin film of magnetic material can be carried out like the method of forming the thin film of gold as described below, except that the magnetic material is used instead of gold.

The multifunctional nanoparticles according to the present invention may be prepared through a preparation method comprising the steps of: (1) loading a drug into a polymer to prepare polymer nanoparticles; (2) depositing a portion of the surface of the polymer nanoparticles with a gold thin film; (3) conjugating to the gold thin film an antibody to a substance expressed on the surface of the cells to which the drug is to be delivered; (4) separating from the resulting nanoparticles those in which a portion of the surface of the polymer nanoparticles is deposited with the gold thin film and conjugated with the antibody.

The step (1) of the preparation method according to the present invention is a step of loading a drug into a polymer to prepare polymer nanoparticles. A method of preparing polymer nanoparticles having a drug located at the core is known in the art to which the present invention pertains. In the present invention, the polymer nanoparticles can be prepared according to the known method.

The step (2) of the preparation method according to the present invention is a step of depositing a portion of the surface of the polymer nanoparticles with a gold thin film. First, the polymer nanoparticles are dissolved in a solvent, for example, water, to prepare a suspension, and then the suspension is sprayed on a glass or silicon substrate so as to distribute the polymer nanoparticles uniformly. In order to distribute the polymer nanoparticles uniformly on the substrate, the glass or silicon substrate is preferably treated with piranha, such that it is made hydrophilic. This is because the glass or silicon substrate is originally hydrophobic in nature, and thus, when it is sprayed with the polymer nanoparticles, which are dissolved in water to show hydrophilicity, the polymer nanoparticles agglomerate into drops, and thus are not uniformly distributed.

Also, in order to distribute the polymer nanoparticles uniformly on the substrate, and then to deposit a gold thin film uniformly on the polymer nanoparticles, the step (2) is preferably carried out in a state in which the substrate is located on a spin coater. This is because the spin coater spins, and thus acts to fix the polymer nanoparticles arranged on the substrate to predetermined locations, and then allows the gold thin film to be uniformly deposited.

After the polymer nanoparticles are distributed uniformly on the substrate, a gold thin film is deposited on the surface of the polymer nanoparticles. In this case, a thermal evaporator is preferably used. The thermal evaporator heats solid gold in a vacuum state to generate a gold vapor, which becomes solid when it comes in contact with the polymer nanoparticles arranged on the substrate, such that a gold thin film can be deposited on the polymer nanoparticles. This gold thin film is deposited over 10-90% of the entire surface of the polymer nanoparticle.

The nanoparticles deposited with the gold thin film as described above can be separated from the substrate by applying physical force, for example, using ultrasonic waves.

Step (3) of the preparation method according to the present invention is a step of conjugating to the gold thin film an antibody to a substance expressed on the surface of a cell to which the drug is to be delivered. Because the antibody also contains one or more amino acids, including a thiol group, the conjugation between the gold thin film and the antibody can be easily achieved through a covalent bond between the gold or platinum and the thiol group in the antibody.

The step (4) of the preparation method according to the present invention is a step of separating from among the resulting nanoparticles those in which a portion of the surface of the polymer nanoparticles is deposited with the gold thin film and conjugated with the antibody. The antibody-gold thin film-polymer nanoparticles can be separated through, for example, centrifugation, because they are heavier than the gold thin film-polymer nanoparticles. Other separation methods, which can be used in the present invention, include filtration, serum replacement and the like.

In another aspect, the present invention provides a composition for delivering a drug to a target site, the composition comprising the multifunctional nanoparticles according to the present invention and a pharmaceutically acceptable carrier.

The composition according to the present invention can be administered through routes, which are conventionally used in the medical field. Preferably, it can be administered via parenteral routes, for example, intravenous, intra-abdominal, intramuscular, subcutaneous or topical routes.

Carriers, which are used in the present invention, include carriers and vehicles that are conventionally used in the medical field. Pharmaceutically acceptable carriers that can be used in the present invention include, but are not limited to, ion exchangers, alumina, aluminum stearate, lecithin, serum proteins, buffer substances, water, salts, electrolytes, colloidal silica, magnesium trisilicate, polyvinyl pyrrolidone, cellulose-based substances, polyethylene glycol, sodium carboxymethylcellulose, polyacrylates, waxes, polyethylene glycol and wool fat.

In one embodiment, the composition according to the present invention can be prepared in an aqueous solution for parenteral administration. Preferably, Hank's solution, Ringer's solution or a buffered solution such as physically buffered saline may be used. Aqueous injection suspension may contain a substance capable of raising the viscosity of the suspension, such as sodium carboxymethyl cellulose, sorbitol or dextran.

The preferred compositions of the present invention may be in the form of a sterile injectable preparation, for example, as a sterile injectable aqueous solution or suspension. This suspension may be formulated according to techniques known in the art using suitable dispersing or wetting agents along with suspending agents. The sterile injectable preparation may also be a sterile injectable solution or suspension in a non-toxic parenterally-acceptable diluent or solvent. Among acceptable vehicles and solvents that may be employed are mannitol, water, Ringers solution and isotonic sodium chloride solution. In addition, sterile, fixed oils are conventionally employed as a solvent or suspension medium. For this purpose, any bland fixed oil may be employed, including synthetic mono- or diglycerides.

In stiff another aspect, the present invention provides a therapeutic method, comprising the steps of: (1) injecting into a subject a composition for delivering a drug to a target site, the composition comprising the invention multifunctional nanoparticles and a pharmaceutically acceptable carrier, (2) allowing the multifunctional nanoparticles to be concentrated at the target site; and (3) irradiating the target site with near-infrared light to generate heat, so as to kill cells present in the target site and accelerate the release of the drug to treat the target site.

In the step (1) of the therapeutic method, a composition for delivering a drug to the target site, the composition comprising the inventive multifunctional nanoparticles and a pharmaceutically acceptable carrier, is injected into a subject. In this step, information about the subject's disease and the site (target site) to which a drug is to be delivered, is determined through preliminary examination, for example, blood or urine examination, and the multifunctional nanoparticles prepared based on such information are provided with an antibody to a substance present in the cells to which the drug is to be delivered.

In the step (2) of the therapeutic method, the multifunctional nanoparticles injected through the step (1) move through blood vessels, and with the passage of time, they are concentrated at cells (i.e., target site) to which the drug is to be delivered, because the multifunctional nanoparticles comprise the antibody to the substance present in the cells to which the drug is to be delivered.

In the step (3) of the therapeutic method, when the target site is irradiated with near-infrared light (800-1200 nm), the gold thin film of the multifunctional nanoparticles absorbs near infrared light, and then generates heat. The heat can kill cells in the target sites and sites adjacent thereto, and also promotes the degradation of the polymer to accelerate the release of the drug included in the polymer. As a result, it is possible to double the desired therapeutic effect in the target site through the killing of cells by heat itself and the acceleration of drug release by heat.

Meanwhile, if the multifunctional nanoparticles according to the present invention comprise: polymer nanoparticles, formed by loading a drug into a polymer; a thin film of magnetic material deposited on the surface of the polymer nanoparticles; a gold thin film deposited on the surface of the magnetic thin film; and an antibody to a substance expressed on the surface of a cell to which the drug is to be delivered, the antibody being conjugated to the surface of the gold thin film, then the multifunctional nanoparticles may be used for the diagnosis and treatment of disease as described below.

That is, the present invention provides a method for the diagnosis and treatment of disease, the method comprising the steps of: (1) injecting into a subject a composition for delivering a drug to a target site, the composition comprising the above-described multifunctional nanoparticles and a pharmaceutically acceptable carrier; (2) sensing a signal emitted by the multifunctional nanoparticles from the subject to determine a target site; and (3) irradiating the target site with near-infrared light to generate heat so as to kill cells present in the target site; and accelerate the release of the drug, thereby treating the target site.

In the step (1) of the diagnostic and therapeutic method, a composition for delivering a drug to a target site, the composition comprising the above-described multifunctional nanoparticles and a pharmaceutically acceptable carrier, is injected into a subject. Prior to this step, information about a subject's disease and the site (target site) to which the drug is to be delivered is determined through preliminary examination, for example blood or urine examination. The multifunctional nanoparticles prepared based on such information are provided with an antibody to a substance present in cells to which the drug is to be delivered, but they have an advantage in that it is possible to identify and diagnose the target site more precisely.

If the method is ended at step (2) after performing step (1), only the diagnosis of the disease can be achieved, and if the method is conducted up to the step (3) after performing steps (1) and (2), both the diagnosis and the treatment of disease can be achieved.

In the diagnosis method, the signal emitted by the multifunctional nanoparticles can be sensed by various systems which use a magnetic field, and such systems may include a magnetic resonance imaging (MRI) system. The magnetic resonance imaging (MRI) system is a system for obtaining images by placing a living body in a potential magnetic field, irradiating the body with electric waves having a specific wavelength so as allow atomic nuclei (such as hydrogen) in the body to absorb energy to reach a high-energy state, stopping the irradiation of the electric waves to allow the energy of atomic nuclei (such as hydrogen) to be emitted, converting the energy into a signal, and processing the signal with a computer. Because the magnetic or electric waves are not blocked by bones, clear, three-dimensional CT images for tumors around hard bones or in the brain or marrow can be obtained at any angle in the longitudinal and transversal directions.

Hereinafter, the present invention will be described in further detail. It will however be apparent to those skilled in the art that these examples are illustrative only, and the scope of the present invention as disclosed in the accompanying claims is not limited thereto.

Example 1

Preparation of Polymer Nanoparticles (A) PS Nanoparticles

For PS nanoparticles, PS beads having a diameter of 100 nm, purchased from Aldrich Chemicals Co., were used.

(B) PLGA Nanoparticles

PLGA nanoparticles were prepared in the following manner. 100 mg of PLGA 50:50 (molecular weight of 5,000; Wako Chemicals Co.) was dissolved in 10 ml of chloroform (Duksan Pure Chemicals Co.). The solution was added to 20 ml of an aqueous phase containing polyvinyl alcohol (molecular weight of 15,000-20,000) as a stabilizer. After mutual saturation of organic and continuous phases, the mixture was emulsified with an ultrasonic system at 350 W for 10 minutes. Then, the solvent was evaporated, and the remaining material was subjected to serum replacement in filter cells with stirring, and was centrifuged three times at 10,000 rpm for 30 minutes each time, thus obtaining PLGA nanoparticles. The PLGA nanoparticles thus obtained were analyzed through direct light scattering analysis and, as a result, the PLGA nanoparticles had an average diameter of about 100 nm.

Example 2

Deposition of Gold Thin Film on Polymer Nanoparticles

The PS nanoparticles and the PLGA nanoparticles, obtained in Example 1, were dissolved in water to prepare suspensions of the polymer nanoparticles. After a piranha-treated silicon substrate was located in a spin coater, each of the suspensions was sprayed on the surface of the substrate, such that the polymer nanoparticles were distributed uniformly. Then, a gold thin film was deposited on a portion of the surface of the polymer nanoparticles using a thermal evaporator. Following this, the substrate was treated with ultrasonic waves (40 kHz) for about 5-10 minutes, and then the gold thin film-deposited polymer nanoparticles were separated from the substrate.

Figure 2A:
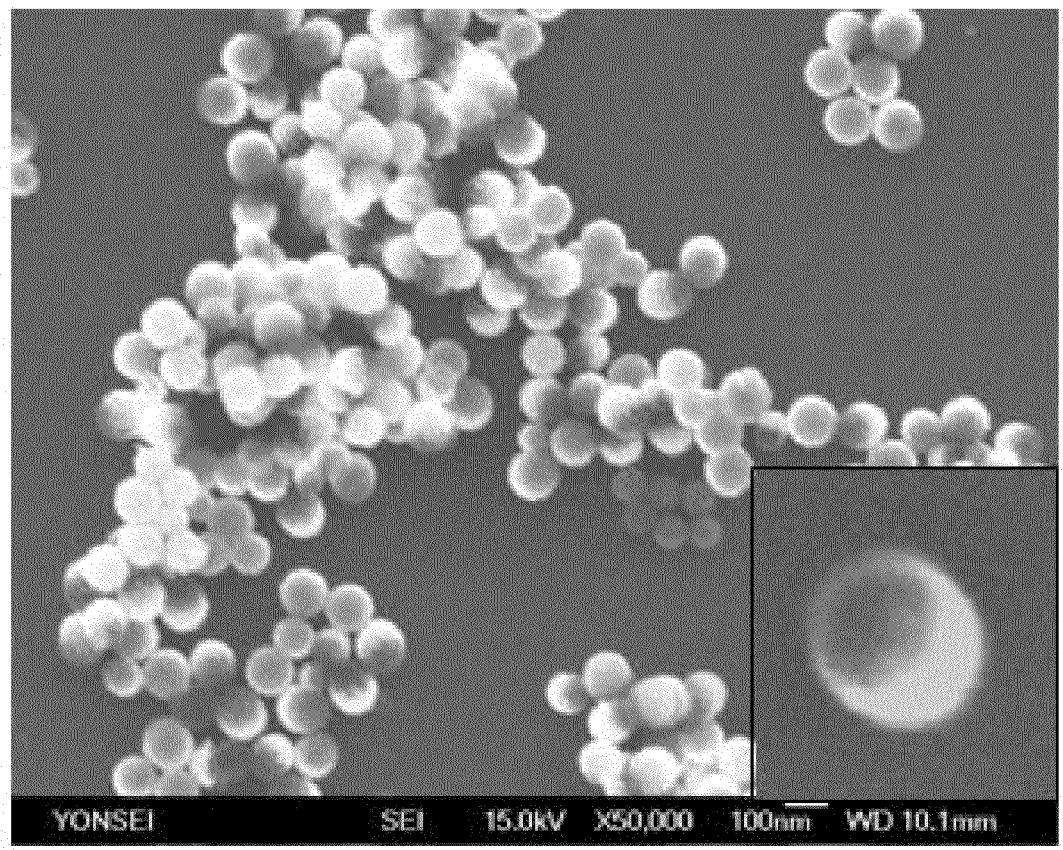
FIG. 2A shows an FESEM image of gold thin film-PS nanoparticles according to the present invention.
Figure 2B:
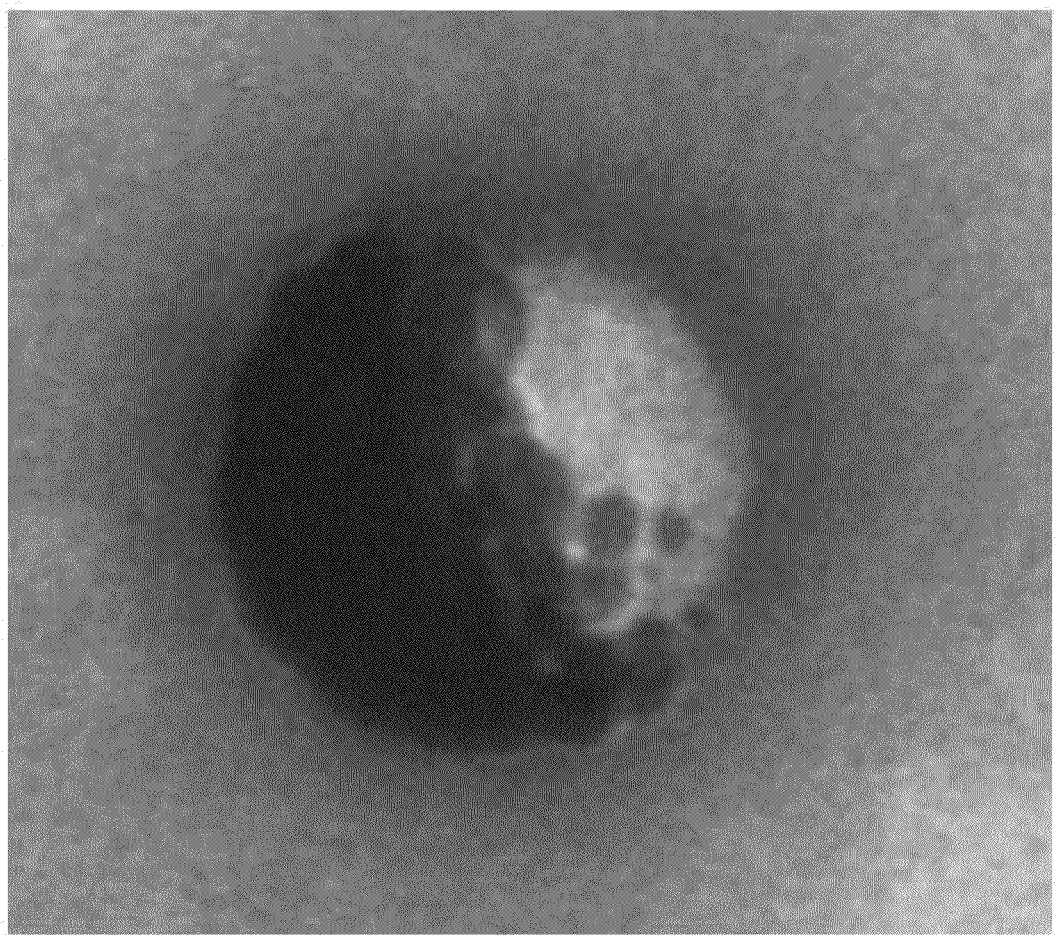
FIG. 2B shows a TEM image of gold thin film-PLGA nanoparticles according to the present invention.

The gold thin film-deposited PS nanoparticles thus obtained were observed through FESEM (Field Emission Scanning Electron Microscopy). As a result, as shown in FIG. 2A, it could be seen that the gold thin film was deposited on a portion of the surface of the PS nanoparticles. Likewise, the above-obtained PLGA nanoparticles were observed through TEM and, as a result, as can be seen in FIG. 2B, the gold thin film was deposited on a portion of the surface of the PLGA nanoparticles.

Example 3

Absorption Spectrum Analysis of Gold Thin Film-Nanoparticles According to the Present Invention The absorption spectra of the gold thin film-PS nanoparticles and the gold thin film-PGLA nanoparticles, obtained in Example 2, were analyzed using UV-Vis/NIR spectrophotometry.

Figure 3:
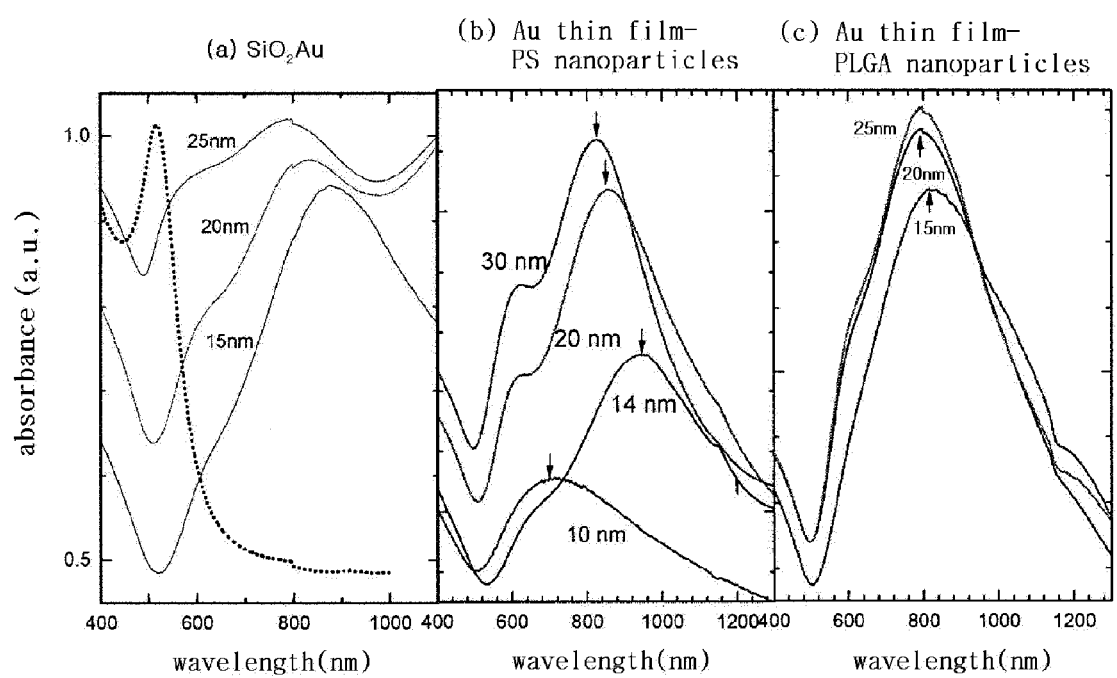
FIG. 3 shows the change in the optical absorption spectrum with gold thin film thickness of (a) silica nanoparticles having a gold thin film deposited on a portion of the surface thereof, (b) gold thin film-PS nanoparticles according to the present invention, and (c) gold thin film-PLGA nanoparticles according to the present invention.

First, a gold thin film was deposited on a portion of the surface of silica nanoparticles, and the absorption spectrum of the nanoparticles was analyzed. As shown in FIG. 3(a), despite having asymmetrical geometry, the silica nanoparticles having the gold thin film deposited on a portion of the surface thereof showed properties similar to those of silica nanoparticles having a gold thin film deposited on the entire surface thereof. In particular, as the thickness of the gold thin film was varied, the absorption peak was shifted to the NIR range.

(A) Gold Thin Film-PS Nanoparticles

As shown in FIG. 3(b), the absorption peak of the gold thin film-PS nanoparticles was changed depending on the thickness of the gold thin film, like the silica nanoparticles having the gold thin film deposited on a portion of the surface thereof. If the thickness of the gold thin film was more than 14 nm, the absorption peak could be shifted to the near infrared range, whereas, if the thickness was less than 14 nm, the absorption peak was shifted to shorter wavelengths.

(B) Gold Thin Film-PLGA Nanoparticles

The absorption spectra of gold thin film-PLGA nanoparticles having various gold thin film thicknesses were analyzed, and the analysis results are shown in FIG. 3(c). The absorption peaks of the nanoparticles were located within the NIR range, but the peak position thereof was not greatly changed with the change in the thickness of the gold thin film. However, FIG. 3(c) shows that NIR light can be absorbed by the gold thin film-PLGA nanoparticles, such that it can be converted to thermal energy. The degradation rate of PLGA varies depending on temperature (Dunne, M. et al. *Biomaterials*, 2000, vol. 21 P. 1659), and the photothermal conversion in the gold thin film can accelerate the degradation rate of PLGA, resulting in an increase in drug release rate.

Example 4

Figure 4A:
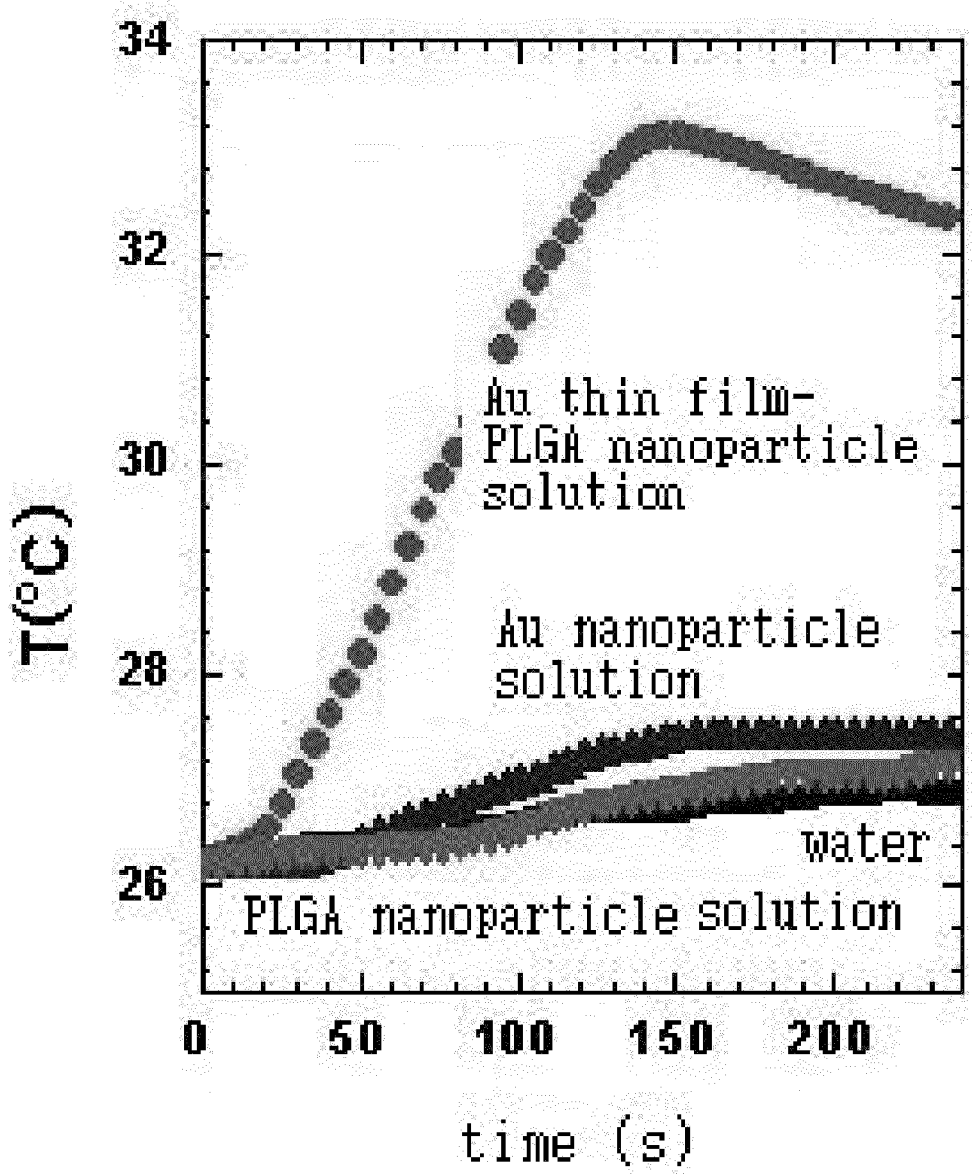
FIG. 4A shows whether gold thin film-PLGA nanoparticles according to the present invention undergo photothermal conversion.

Analysis of Whether Gold Thin Film-PLGA Particles Perform Photothermal Conversion Gold thin film-PLGA nanoparticles having a size of 25 nm were dissolved in triple distilled water at a concentration of 145 μg/ml. The solution was irradiated with a coherent diode laser (λ=808 nm) at an output of 7 W/cm$^2$ for 2 minutes, and then the temperature of the solution was measured using a thermocouple for 4 minutes. As shown in FIG. 4A, the temperature of the solution containing the gold thin film-PLGA nanoparticles was increased from 26.3° C. to 33.1° C. under NIR radiation. For comparison, pure water, a solution of PLGA nanoparticles (3.3 mg/ml) and a solution of Au nanoparticles (2.71 mg/ml) were also irradiated with NIR as described above, but the temperature thereof was not substantially increased. Such results indicate that the gold thin film-PLGA nanoparticles of the present invention can convert near-infrared photoenergy to thermal energy.

Figure 4B:
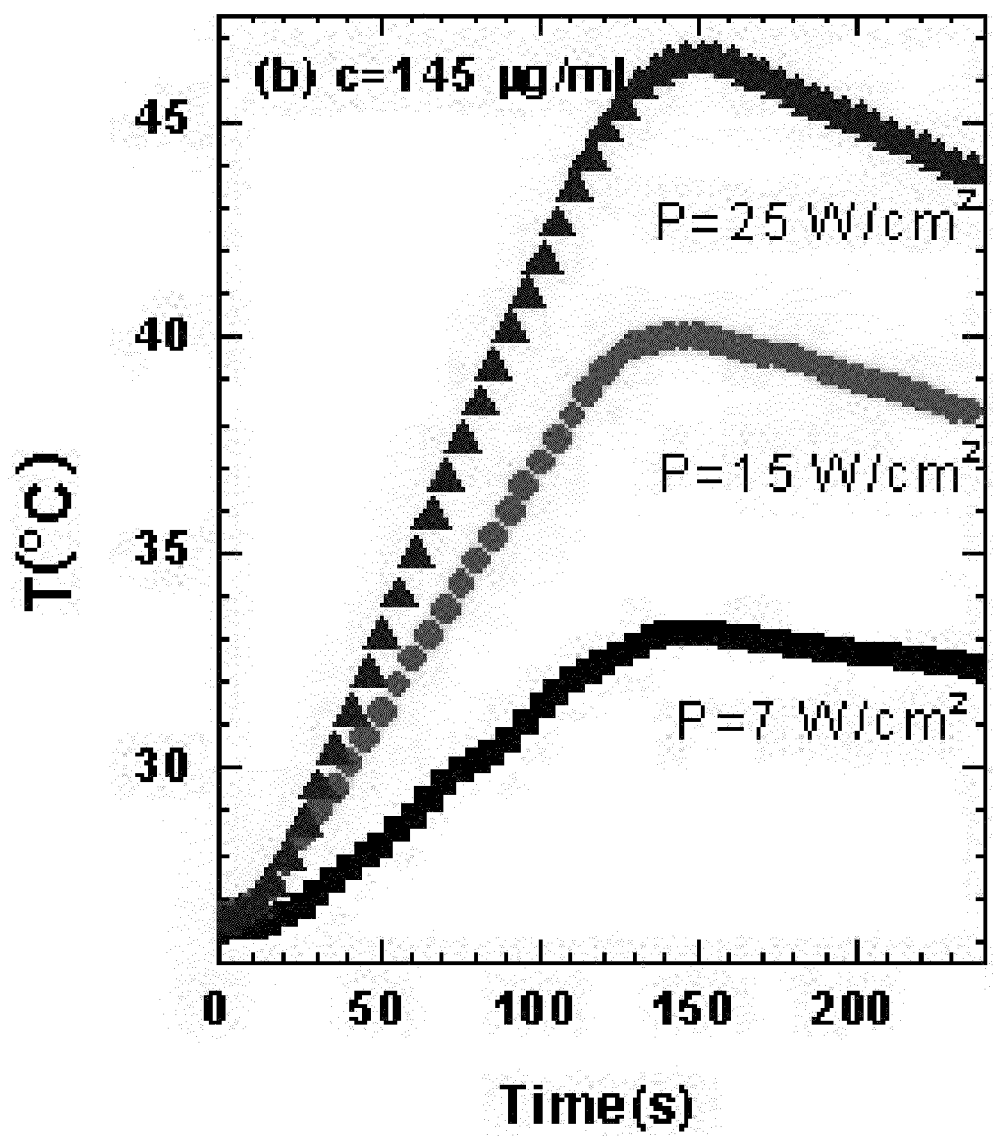
FIG. 4B shows the effect of the output of optical energy on the photothermal conversion of gold thin film-PLGA nanoparticles according to the present invention.

Also, the solution containing the gold thin film-PLGA nanoparticles at a concentration of 145 μg/ml was irradiated with a coherent diode laser (λ=808 nm) at each of outputs of 7 W/cm$^2$, 15 W/cm$^2$ and 25 W/cm$^2$ for 2 minutes each, and then the temperature of the solution was measured using a thermocouple for 4 minutes. As shown in FIG. 4B, as the output was increased, the temperature of the solution was also increased.

Figure 4C:
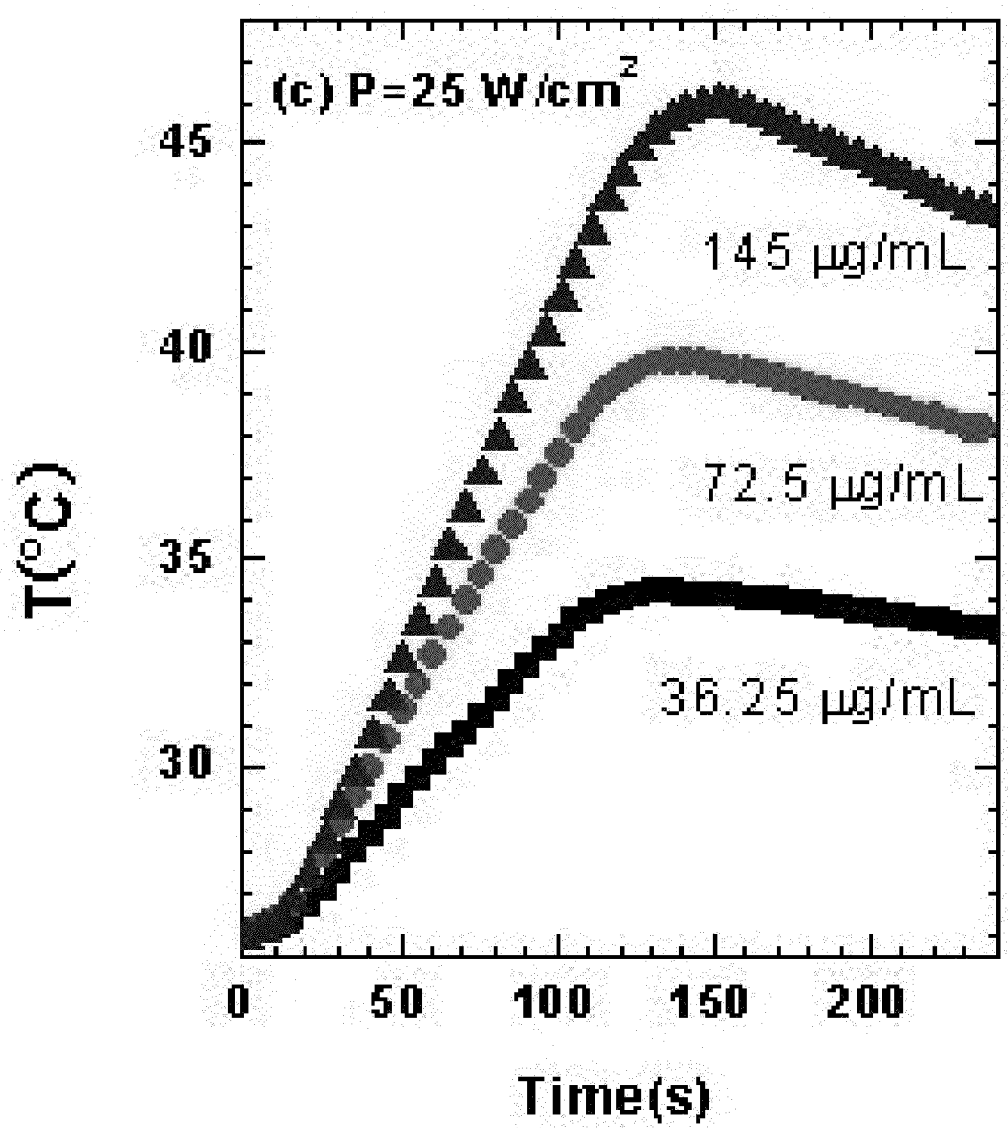
FIG. 4C shows the effect of the concentration of the inventive gold thin film-PLGA nanoparticles on the photothermal conversion of the gold thin film-PLGA nanoparticles.

In addition, the gold thin film-PLGA nanoparticles were dissolved at each of concentrations of 36.25 μg/ml, 72.5 μg/ml and 145 μg/ml. The solutions were irradiated with a coherent diode laser (λ=808 nm) at an output of 25 W/cm$^2$ for 2 minutes, and then the temperatures of the solutions were measured using a thermocouple for 4 minutes. As shown in FIG. 4C, as the concentration of the gold thin film-PLGA nanoparticles was increased, the temperature of the solution was also increased.

Example 5

Preparation of Antibody-Conjugated Gold Thin Film-PLGA Nanoparticles

A CD4 antibody capable of targeting the lymphoma cell line H9 was conjugated to the gold thin film-PLGA nanoparticles. Specifically, the gold thin film-PLGA nanoparticles and the antibody were added to phosphate buffer saline (pH 7.4), and then the particles were dispersed using ultrasonic waves. Then, 1% PEG (polyethylene glycol) solution, contributing to the stabilization of the particles, was added thereto, and the resulting solution was left to stand at 4° C. for one day. By doing so, the CD4 antibody was conjugated to the gold thin film through a covalent bond between the gold and the thiol group in the CD4 antibody. The conjugation reaction product was centrifuged three times at 10,000 rpm for 3 minutes each time to remove antibody-unconjugated gold thin film-PLGA nanoparticles.

Figure 5A:
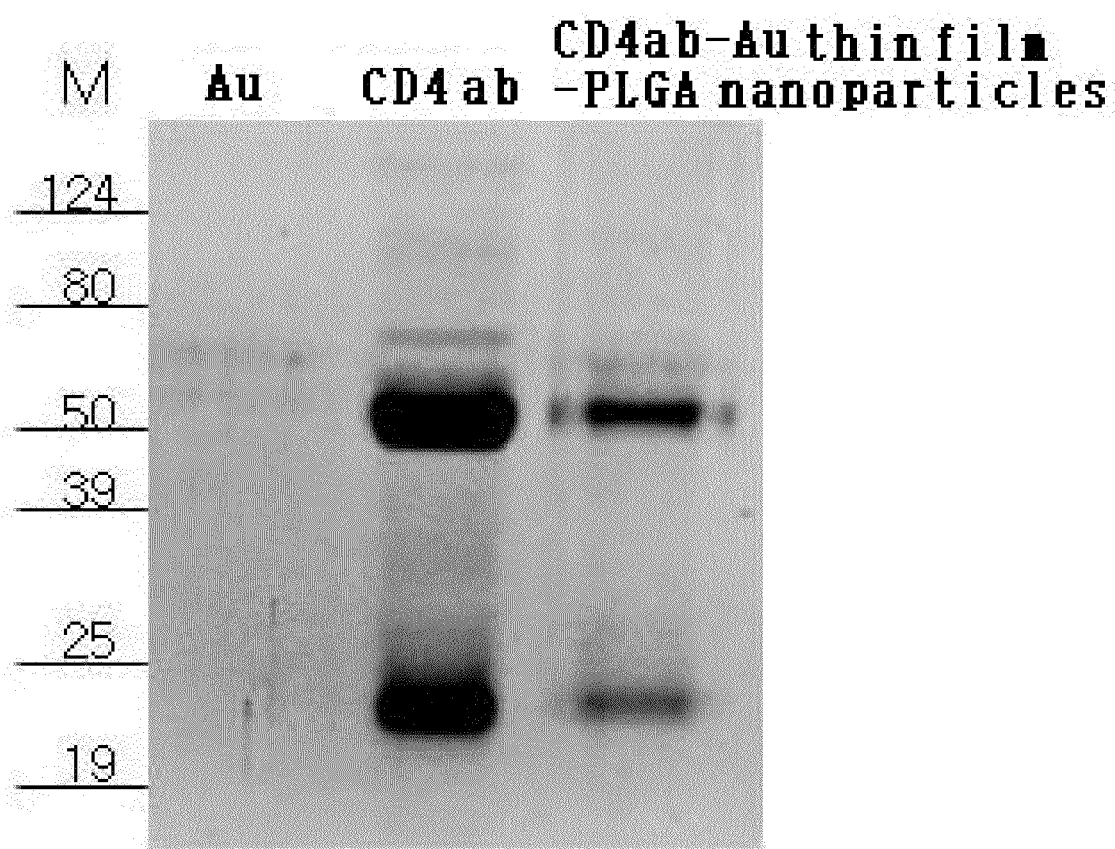
FIG. 5A shows the results of SDS-PAGE analysis, performed to determine whether an antibody was conjugated to the inventive gold thin film-PLGA nanoparticles.
Figure 5B:
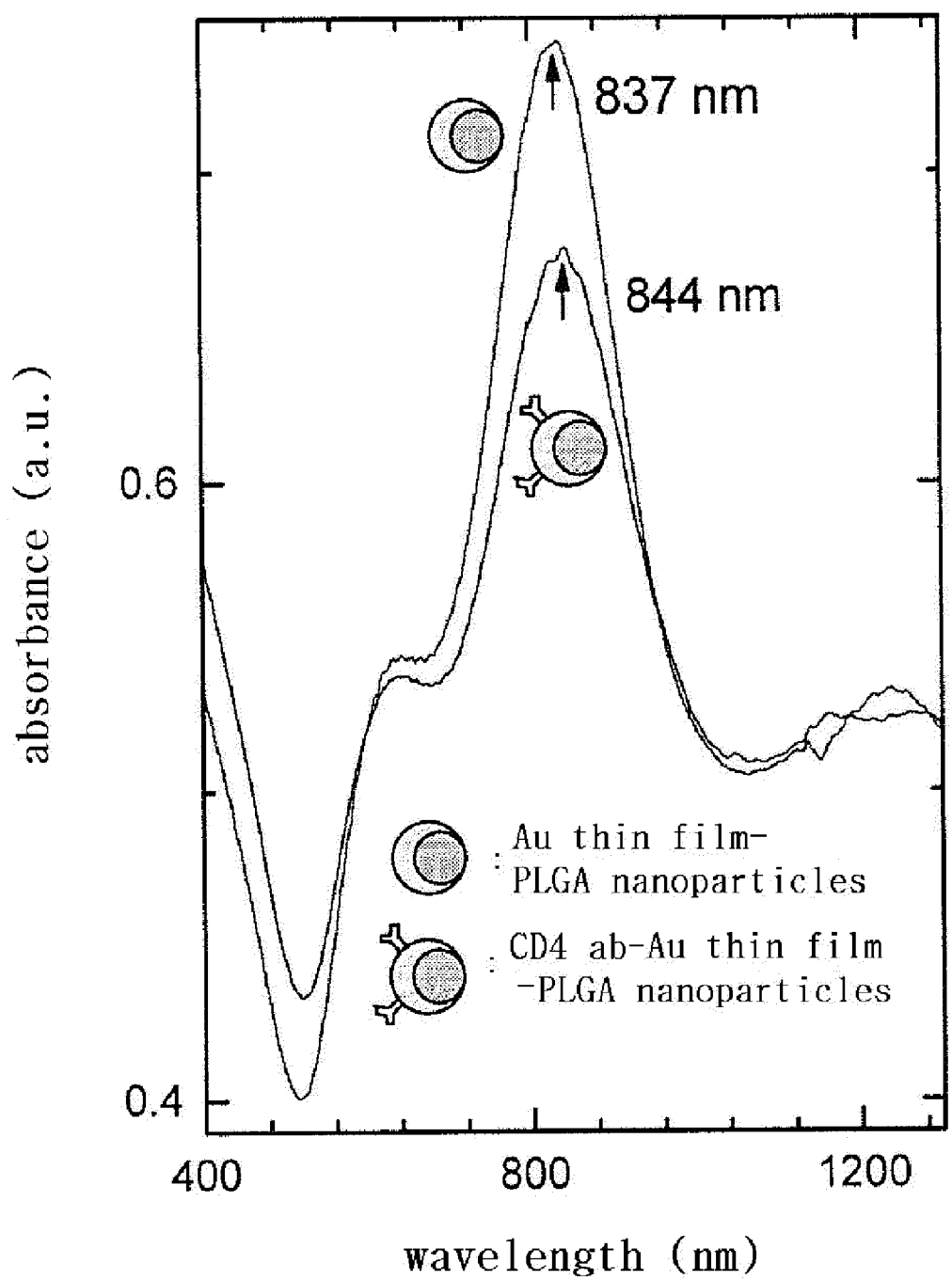
FIG. 5B shows the optical absorption spectra of the inventive gold thin film-PLGA nanoparticles, before and after the nanoparticles are conjugated with a CD4 antibody.

In order to confirm whether the antibody was conjugated to the gold thin film, the above-obtained antibody-gold thin film-PGA nanoparticles were washed with phosphate buffer saline (pH 7.4) and boiled in SDS sample buffer. The resulting product was separated on 10% SDS-PAGE and stained with Coomassie blue solution to visualize the bands. The analysis results are shown in FIG. 5A, from which it can be seen that the antibody was conjugated to the gold thin film. In addition, the absorption spectrum of the antibody-conjugated multifunctional nanoparticles was analyzed and, as a result, it can be seen that the absorption spectrum is almost the same as the absorption spectrum measured before the antibody was conjugated (see FIG. 5B).

Example 6

Figure 6A:
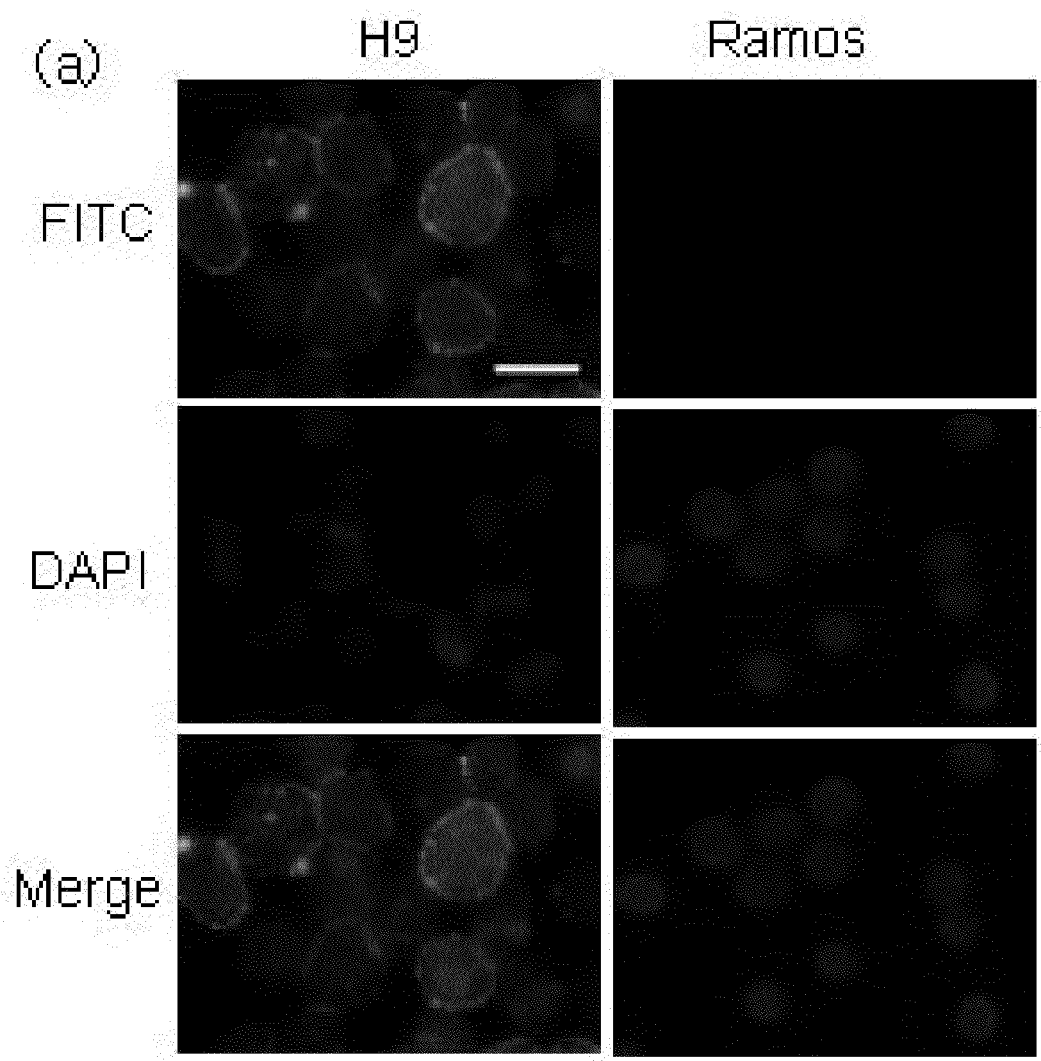
FIG. 6A is a fluorescent microscope image showing CD4 antibody-gold thin film-PLGA nanoparticles according to the present invention bound specifically to H9 cells (left column: H9 cell line; and right column: Ramos cell line).

Targeting of Antibody-Conjugated Multifunctional Nanoparticles According to the Present Invention In order to confirm whether the antibody-conjugated nanoparticles obtained in Example 4 bind to the desired target, H9 cells (American Type Culture Collection), which express CD4 molecules, and the multifunctional nanoparticles were left to stand for 30 minutes, stained with FITC-conjugated goat anti-mouse Ig (BD Phanningen), and then observed under a fluorescent microscope AXIOVERT200 (Carl Zeiss). At this time, as a control group, Ramos cells of the human B cell line were used instead of the H9 cells expressing the CD4 molecules, and were subjected to the same procedure described above. The results of the microscope observation are shown in FIG. 6A, from which it can be seen that the multifunctional nanoparticles according to the present invention bound specifically to the H9 cells expressing the CD4 molecules (left column of FIG. 6A), whereas they did not bind to the Ramos cells not expressing the CD4 (right column of FIG. 6A).

Figure 6B:
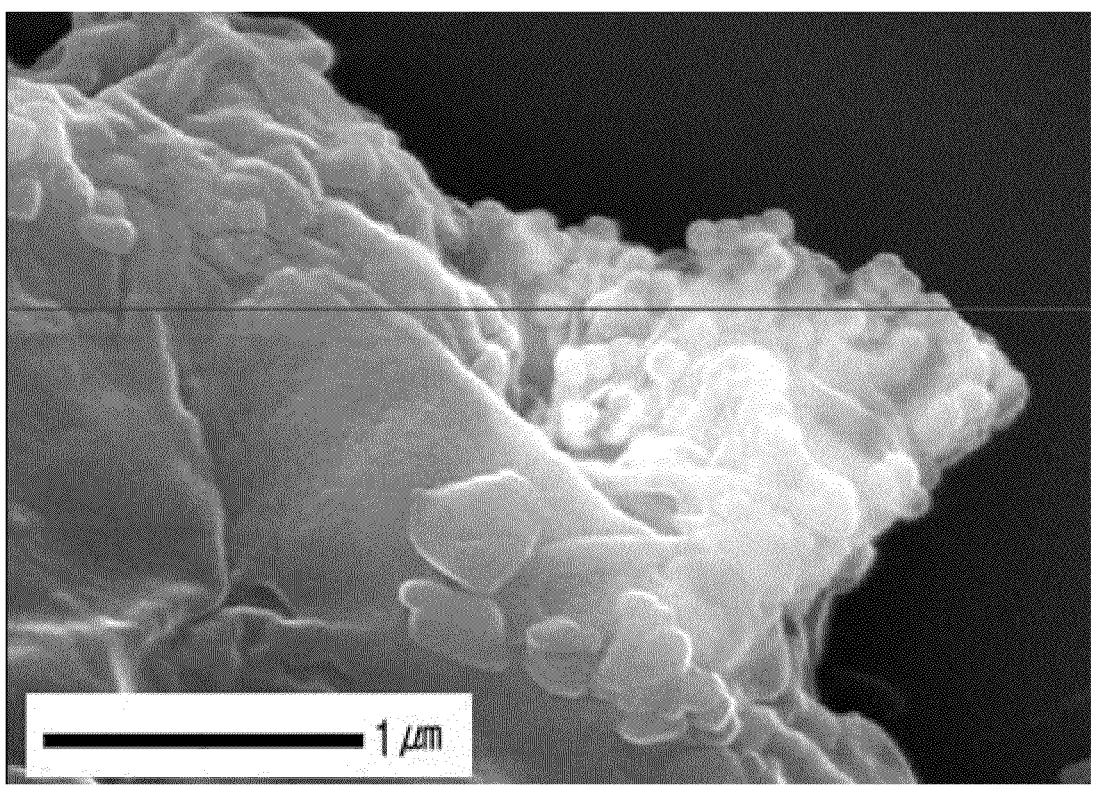
FIG. 6B is an FESEM image showing CD4 antibody-gold thin film-PLGA nanoparticles according to the present invention bound specifically to H9 cells.
Figure 6C:
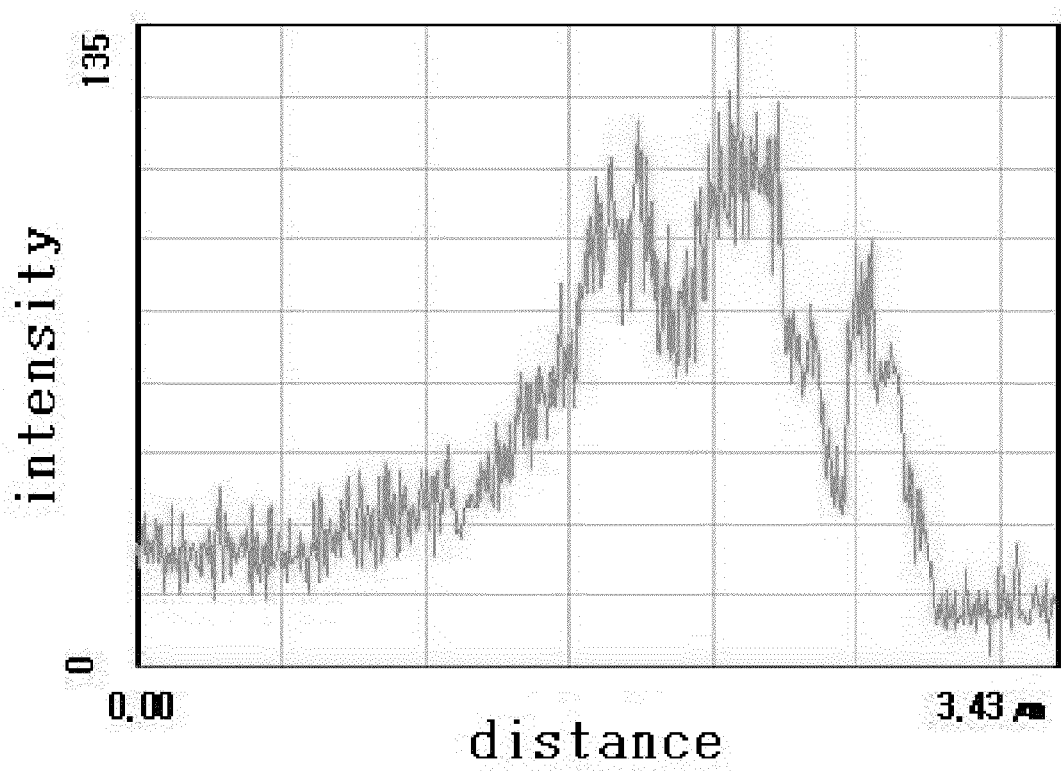
FIG. 6C is an EXD image showing CD4 antibody-gold thin film-PLGA nanoparticles according to the present invention bound specifically to H9 cells.

In addition, the multifunctional nanoparticles were observed with FESEM, and the observation results are shown in FIG. 6B, from which it can be seen that the multifunctional nanoparticles according to the present invention bound specifically to the H9 cells. It was further confirmed through EDX (Dispersive X-Ray) analysis that those bound to the H9 cells as shown in FIG. 6B were the inventive multifunctional nanoparticles (see FIG. 6C).

Example 7

Preparation of Gold Thin Film-Olga Nanoparticles According to the Present Invention To easily analyze the drug release pattern of the gold thin film-PLGA nanoparticles according to the present invention, rhodamine-loaded gold thin film-PLGA nanoparticles were prepared using rhodamine instead of a drug. For this purpose, PLGA 50:50 (100 mg; Mw. 20,000; Wako Chemicals) and rhodamine (4 mg; Mw. 443; Sigma Aldrich) were dissolved in 10 ml of chloroform. The solution was added to 20 ml of an aqueous phase containing polyvinyl alcohol (Mw. 15,000-20, 000; Aldrich Chemical Co.) as a stabilizer. After mutual saturation of organic and continuous phases, the mixture was emulsified using an ultrasonic system at 350 W for 10 minutes. Then, the solvent was evaporated, and the remaining material was subjected to serum replacement in filter cells and centrifuged three times at 10,000 rpm for 30 minutes each time, thus obtaining rhodamine-loaded gold thin film-PLGA nanoparticles (hereinafter, referred to as "gold thin film-PLGA-rhodamine nanoparticles"). The nanoparticles had an average diameter of about 100 nm as analyzed by direct light scattering analysis, and had a glass transition temperature of about 42 as measured by a differential scanning calorimeter (TA Instrument DSC SDT-600).

Herein, the amount of loaded rhodamine was measured in the following manner: Dried gold thin film-PLGA-rhodamine nanoparticles were added to a phosphate buffer solution (pH 7.4), and the suspension was stirred and ultrasonically treated to extract rhodamine from the nanoparticles. The amount of the extracted rhodamine was measured using a UV spectrophotometer (UV16A, Shimadzu, Japan). Encapsulation efficiency, which is defined as the percentage of the amount of rhodamine encapsulated with the nanoparticles relative to the amount of rhodamine added in the initial stage, was evaluated to be about 4.5%.

Example 8

Analysis of Rhodamine Release Pattern of Gold Thin Film-PLGA-Rhodamine Nanoparticles According to the Present Invention The gold thin film-PLGA-rhodamine nanoparticles were dissolved in triple distilled water at a concentration of 200 μg/ml, and 5 ml of the solution was loaded into a dialysis tube equipped with a cut-off membrane having a molecular weight of 10,000 Da. The tube was placed in a transparent vial filled with 4 ml of deionized water. The tube was irradiated with a coherent diode laser at an output of 7 W/cm$^2$ at room temperature at 1-min intervals.

Figure 7A:
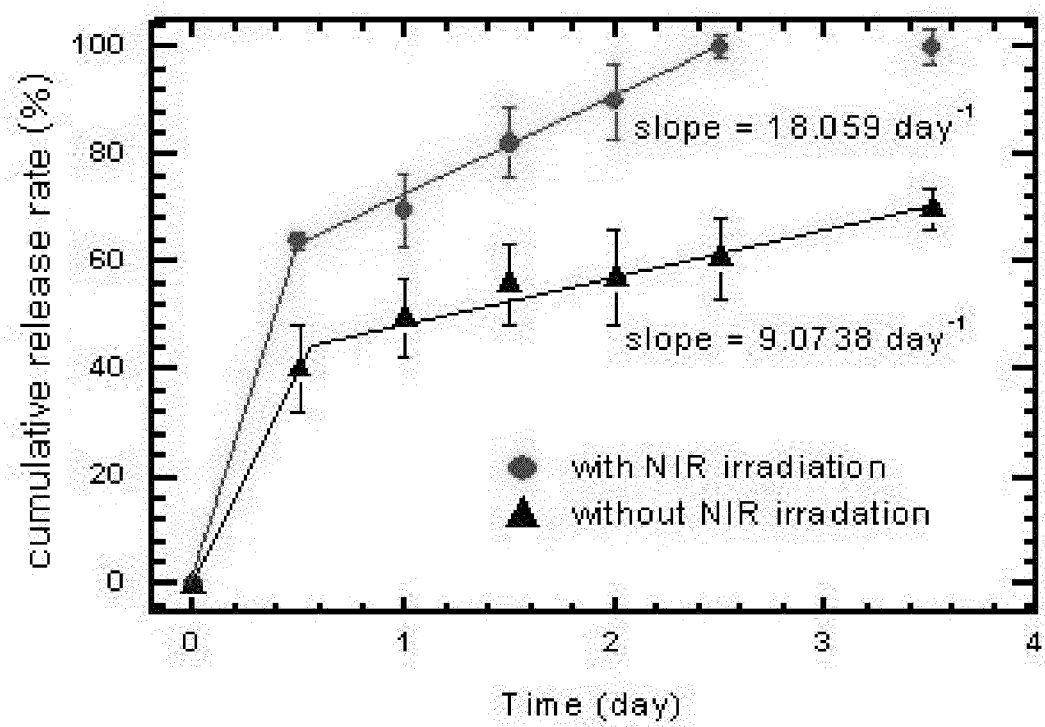
FIG. 7A shows the results of UV spectrophotometry conducted to measure the patterns of release of rhodamine from the inventive gold thin film-PLGA-rhodamine nanoparticles in the presence and absence of NIR radiation.

The release of rhodamine was measured using a UV spectrophotometer. As shown in FIG. 7A, a two-step release pattern, including an explosive release step and a zero-order release step, was shown. When NIR radiation was absent, the zero-order rate constant calculated from the slope of cumulative release rate with the passage of time was about 9.1/day, and in the presence of NIR radiation, it was about 18.1/day. The release rate in the presence of NIR radiation was about two times higher than in the absence of NIR radiation. Also, in the presence of NIR radiation, most of the rhodamine was released within 3 days, whereas, in the absence of NIR radiation, about 60% of the rhodamine was released.

Figure 7B:
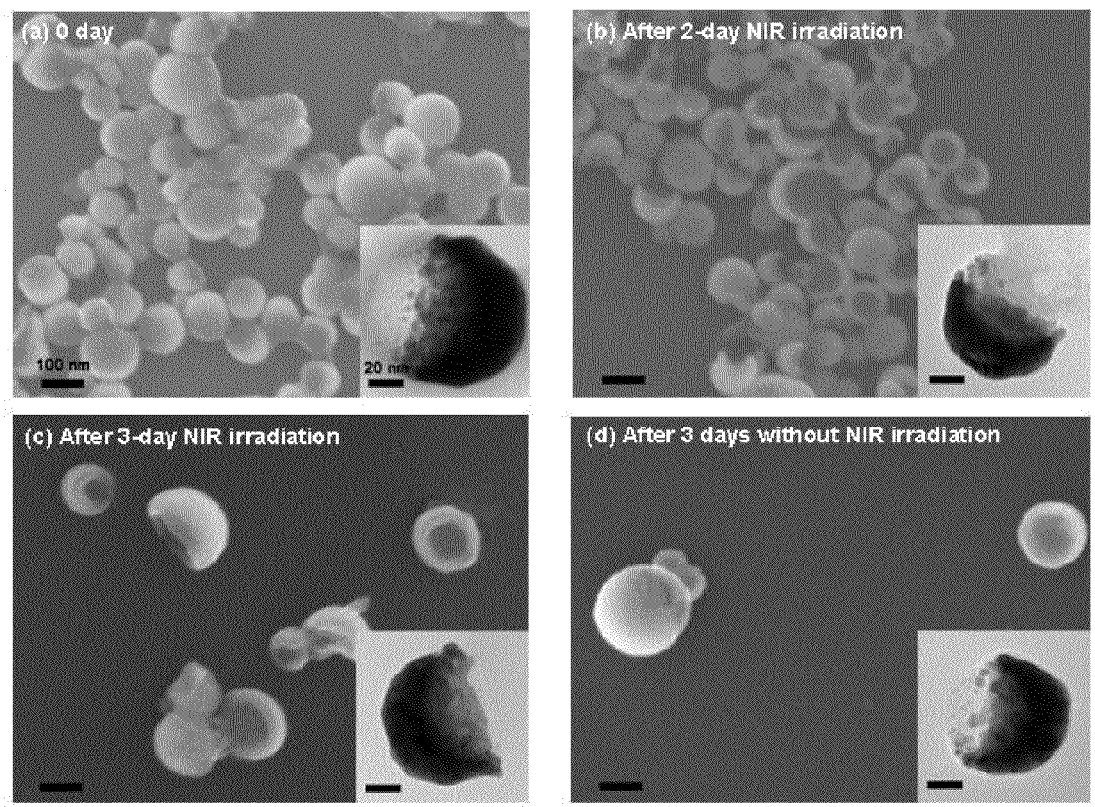
FIG. 7B illustrates an FESEM image and a TEM image (right lower portion), which show the patterns of degradation of a PLGA polymer in the inventive gold thin film-PLGA-rhodamine nanoparticles in the presence and absence of NIR radiation.

The images of the nanoparticles before NIR radiation, after NIR radiation for 2 days and after NIR radiation for 3 days were observed with FESEM and TEM (right lower image), and the observation results are shown in FIG. 7B. After NIR radiation for 3 days, the portion of PLGA of the gold thin film-PLGA-rhodamine nanoparticles that was not deposited with the gold thin film was rapidly degraded, and the nanoparticles that were not irradiated with NIR maintained their shape even after 3 days.

These results suggest that the release of a drug from the multifunctional nanoparticles according to the present invention can be controlled using NIR light.

Example 9

Figure 8A:
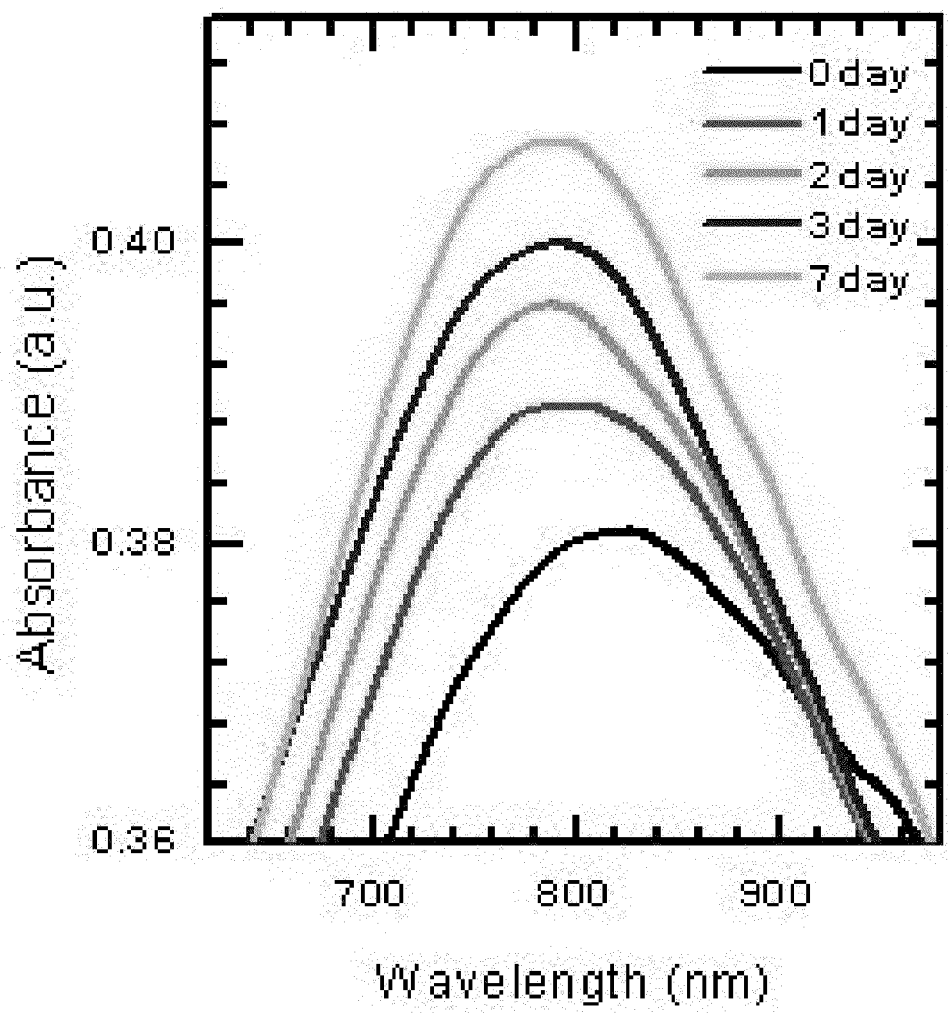
FIG. 8A shows the optical absorption spectra of the inventive gold thin film-PLGA-rhodamine nanoparticles at various NIR radiation times.

Analysis of Optical Properties and Photothermal Conversion of Gold Thin Film-PLGA-Rhodamine Nanoparticles According to the Present Invention The absorption spectrum of the solution obtained in Example 8 was analyzed with an UV-V is/NIR spectrophotometer. As shown in FIG. 8A, before NIR radiation, the absorption peak was located at 823 nm, but, as the NIR radiation time was increased, it was shifted to shorter wavelengths. After 3 days, it was maintained at a constant level. This suggests that, because PLGA is completely degraded within 3 days under NIR radiation, the surface plasmon-resonance peak of the nanoparticles, from which PLGA was removed, was about 783 nm.

Figure 8B:
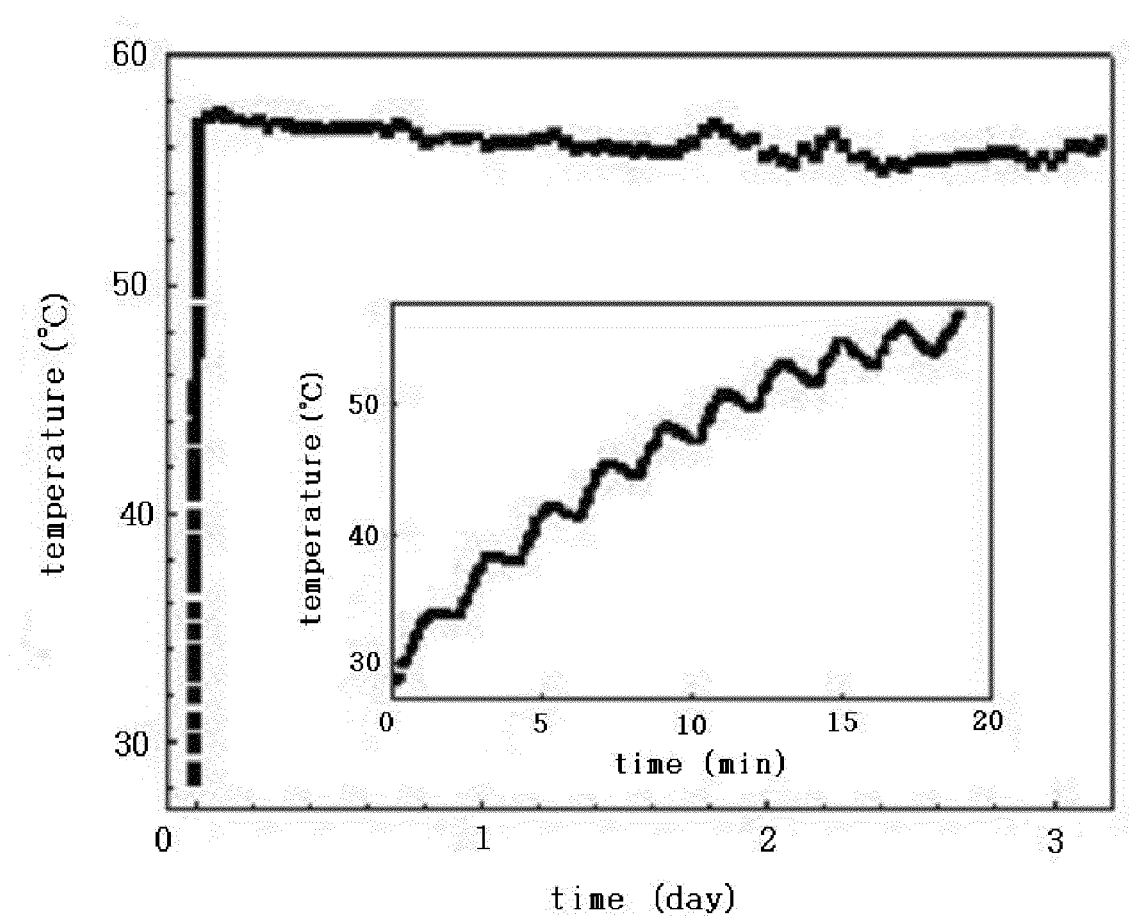
FIG. 8B shows the photothermal conversion of the inventive gold thin film-PLGA-rhodamine nanoparticles at various NIR radiation times.

Also, in order to confirm whether the rhodamine-gold thin film-PLGA nanoparticles underwent photothermal conversion, the temperature of said solution was measured. As shown in FIG. 8B, when a laser was radiated to the solution of the rhodamine-gold thin film-PLGA nanoparticles at a 1-min interval, the solution temperature was periodically increased in the initial stage. After NIR was radiated for about 20 minutes, the solution temperature was rapidly increased to about 57, and was constantly maintained at that temperature for 3 days.

Example 10

Preparation of Gold Thin Film-PS-Nanoparticles Deposited with Mn as Magnetic Substance, and Analysis of Photothermal Conversion and Usability as MRI Contrast Agent Thereof PS-nanoparticles deposited only with a Mn thin film were prepared in the same manner as in Example 2, except that Mn, instead of gold, was deposited on the PS nanoparticles obtained in Example 1. Meanwhile, gold thin film-PS-nanoparticles additionally deposited with a Mn thin film (hereinafter, referred to as "gold/Mn thin film-PS nanoparticles") were prepared by depositing a Mn thin film using Mn according to the procedure of Example 2 and depositing a gold thin film using gold according to the procedure of Example 2. Herein, the gold thin film was formed to varying thicknesses of 15 nm, 25 nm and 35 nm.

Figure 9A:
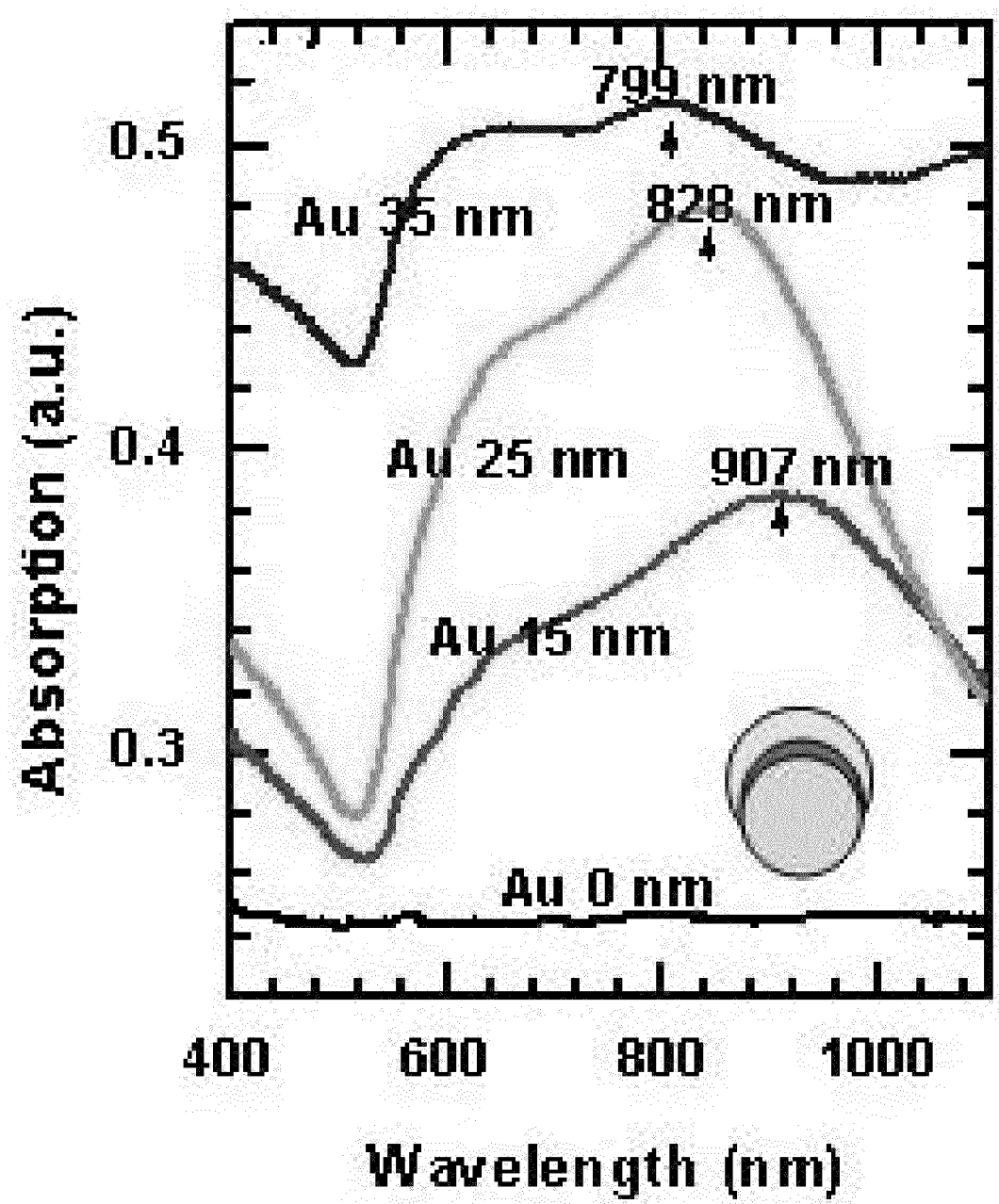
FIG. 9A shows the change in the optical absorption spectrum with gold thin film thickness of gold/Mn thin film-PS nanoparticles according to the present invention.

The absorption spectra of the nanoparticles were analyzed using an UV-Vis/NIR spectrophotometer. As shown in FIG. 9A, in the case of Au (0 nm)/Mn (10 nm), no surface plasmon-resonance peak was observed at 400-1100 nm. In the case of Au (15 nm)/Mn (10 nm), the absorption peak was found at about 907 nm, and, as the thickness of Au was increased, the absorption peak was shifted to shorter wavelengths, like the case of the gold/Mn thin film-PS nanoparticles. This suggests that the surface plasmon resonance peak of the gold/Mn thin film-PS nanoparticles is located in the NIR range and that, even in the presence of Mn, the nanoparticles can convert NIR light to heat.

Figure 9B:
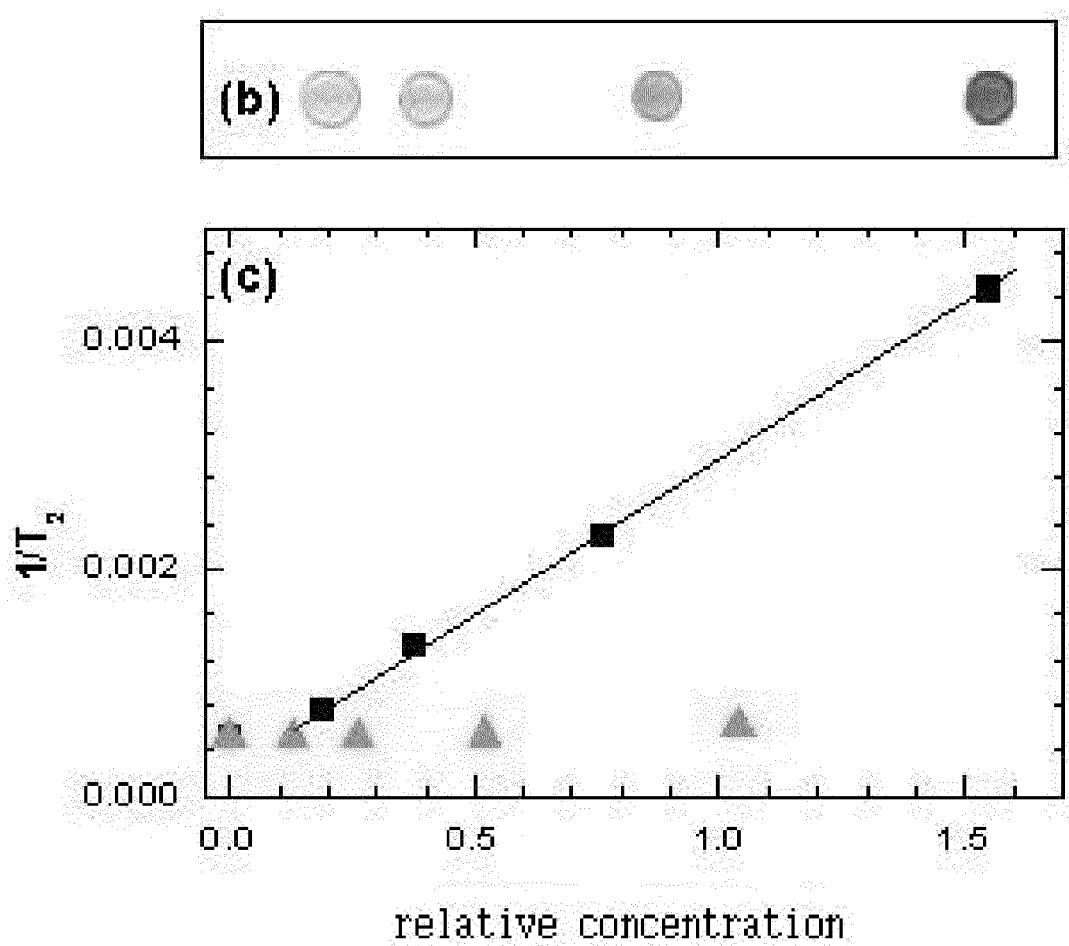
FIG. 9B shows spin-spin relaxation time (T2)-weighted spin echo images (upper portion) and 1/T2 measured at 1.5 T (lower portion) for the inventive gold thin film-PS nanoparticles and gold/Mn thin film-PS nanoparticles.

Also, for the gold/Mn thin film-PS nanoparticles and the gold thin film-PS nanoparticles prepared in Example 2, spin-spin relaxation time (T2)-weighted spin echo MRI images (upper portion) and 1/T2 measured at 1.5 T (lower portion) are shown in FIG. 9B. In the case of the gold/Mn thin film-PS nanoparticles, 1/T2 was increased with an increase in the concentration of the nanoparticles, whereas, in the case of the gold-PS nanoparticles lacking Mn, 1/T2 had the same value as that of water, regardless of the concentration. This suggests that the gold/Mn thin film-PS nanoparticles can be used as an MRI contrast agent due to the Mn.

INDUSTRIAL APPLICABILITY

As described above, the multifunctional nanoparticles according to the present invention can be concentrated at the target site by the antibody. When near infrared light is radiated to the target site, the gold thin film generates heat, which can kill cells in the target site and, at the same time, can promote the degradation of the polymer to accelerate the release of the drug, thus doubling the efficiency of the drug.

What is claimed is:

1. A method for preparing multifunctional nanoparticles, the method comprising the steps of:
    (1) loading a drug into a biodegradable polymer to prepare polymer nanoparticles;
    (2) distributing the polymer nanoparticles uniformly on a glass or silicon substrate;
    (3) generating gold vapor from solid gold by a thermal evaporator to contact the gold vapor with the polymer nanoparticles, thereby depositing a gold thin film on a portion of the surface of the polymer nanoparticles; and
    (4) conjugating to the gold thin film an antibody to a substance expressed on a surface of cells to which the drug is to be delivered;
    wherein the gold thin film of the multifunctional nanoparticles maintains its structure after degradation of the biodegradable polymer.

2. The method of claim 1, wherein the biodegradable polymer is selected from the group consisting of polyphosphazene, polylactide, polylactide-co-glycolide, polycaprolactone, polyanhydride, polymaleic acid and its derivatives, polyanhydride oxybutyrate, polycarbonate, polyorthoester, polyethylene glycol, poly-L-lysine, polyglycolide, and copolymers thereof.

3. The method of claim 1, wherein the gold thin film in step (3) is deposited over 10-90% of the entire surface of the polymer nanoparticles.

4. The method of claim 1, wherein the glass or silicon substrate is treated with piranha so as to make the substrate hydrophilic.

5. The method of claim 1, wherein the conjugation of the antibody to the gold thin film in step (4) is achieved through a covalent bond between gold and a thiol group in the antibody.

* * * * *